United States Patent [19]

Harris et al.

[11] Patent Number: 4,716,104

[45] Date of Patent: Dec. 29, 1987

[54] DETECTING PRESENCE OF HCMV-SPECIFIC IGM

[75] Inventors: William J. Harris, Carnoustie, near Dundee; Helena F. Hart, Edinburgh, both of Scotland

[73] Assignee: Cogent Limited, London, England

[21] Appl. No.: 703,535

[22] Filed: Feb. 20, 1985

[30] Foreign Application Priority Data

Feb. 20, 1984 [GB] United Kingdom ............... 8404368

[51] Int. Cl.$^4$ ................. G01N 33/569; G01N 33/577
[52] U.S. Cl. ........................................... 435/5; 435/7; 435/172.2; 435/240.27; 436/518; 436/548; 436/804; 436/811; 935/110
[58] Field of Search ............... 435/5, 7, 68, 34, 172.2, 435/174, 240, 241, 948, 43; 436/518, 530, 540, 548, 527, 513, 804, 811; 424/85-87; 260/112 B, 112 R; 935/11 D

[56] References Cited

U.S. PATENT DOCUMENTS 4,376,110 3/1983 David et al. ..................... 436/513

OTHER PUBLICATIONS

Chemical Abstracts, vol. 97, #21853y, 1983.
Kohler and Milstein, Nature, vol. 256, pp. 495–497, 1975.
Goldstein et al., Infection and Immunity, vol. 38(1), pp. 273–281, 1982.
Pereira et al., Infection and Immunity, vol. 36(3), pp. 924–932, 1982.
S. Sutherland and J. D. Briggs, "The Detection of Antibodies to Cytomegalovirus in the Sera of Renal Transplant Patients by an IgM Antibody Capture Assay", Journal of Medical Virology 11:147–159, (1983).
K. S. Kim et al., "Production and Characterization of Monoclonal Antibodies Specific for a Glycosylated Polypeptide of Human Cytomegalovirus", Journal of Clinical Microbiology, Aug. 1983, pp. 331–343, vol. 18, No. 2.
P. P. Mortimer et al., "Antibody Capture Radioimmunoassay for Anti-Rubella IgM", J. Hyg., Camb. (1981), 86, 139–153.
R. S. Tedder et al., "IgM-Antibody Response to the Hepatitis B Core Antigen in Acute and Chronic Hepatitis B", J. Hyg., Camb., (1981), 86, 163–172.

*Primary Examiner*—Sidney Marantz
*Attorney, Agent, or Firm*—Cushman, Darby & Cushman

[57] ABSTRACT

Monoclonal antibodies reactive to immediate early and/or early HCMV. The detection of antigens (especially HCMV antigens) by concentrating them on a support and reacting them with monoclonal antibody. The support may be a nitrocellulose membrane (immunodot). Alternatively the support may be a bead carrying a different monoclonal antibody, the two antibodies reacting with different epitopic sites on the antigenic protein. The use of HCMV monoclonal antibody in distinguishing between HCMV-specific IgM and IgG.

2 Claims, 6 Drawing Figures

DETECTING PRESENCE OF HCMV-SPECIFIC IGM

The present invention is concerned with monoclonal antibodies, and especially with antibodies against proteins or glycoproteins which are constituents of human cytomegalovirus (HCMV). The term cytomegalovirus (CMV) encompasses a wide variety of closely related viruses of different strains isolated independently from clinical samples. Current technology cannot clearly establish the relationship between different independently isolated strains. Cytomegaloviruses are therefore defined as those viruses derived from human samples or natural sources which exhibit the properties of:

1. Herpes virus family
2. Infected human cell cultures in vitro which, when histologically stained, reveal easily recognisable intranuclear inclusions.

CMV infection is the most important congenital virus infection medically (CID, intrauterine death, prematurity, malformations, somatic and mental retardation). The symptomology of CMV infection is:

Primary infection—neonatal infection, CMV-induced mononucleosis-like syndrome, hepatitis.

Reactivated infection—transfusion fever, post-operative fever, interstitial pneumonia, chorioretinitis, complication of a malignant disease.

A monoclonal antibody of the present invention can be produced by a hybridoma formed by fusion of cells from a mouse myeloma cell line and cells from a mouse previously immunised with HCMV. A cocktail of different monoclonal antibodies may (1) recognise different antigens, or (2) recognise different epitopes, or (3) differ in isotype.

The laboratory diagnosis of congenital CMV infections requires among other things that virus be isolated from newborn within 2 weeks of birth. CMV-infected patients excrete virus for a long time in saliva, urine, sperm, cervical secretions and faeces. Demonstration of the virus requires 3–6 weeks infection of human cells in vitro, often too long a time to delay therapy.

The serological methods (complement fixation, immunofluorescence, radioimmunoassay and ELISA techniques) available at present do not successfully distinguish between CMV-specific IgM and IgG antibody. IgM antibody is indicative of recent infection and hence specific tests for this antibody are essential.

In the scope of the present invention, monoclonal antibodies have been demonstrated to provide excellent methods for the rapid detection of CMV infection, the specific detection of CMV-specific IgM as well as suitable reagents for general serological methods.

Some individual monoclonal antibodies bind to different proteins or glycoprotein constituents of the virus, while others bind to the same or similar proteins or glycoproteins (as defined by their molecular weight) though they recognise different epitopes. Furthermore it has been recognised that this collection consists of antibodies which differ from one another in their isotypes.

A further feature of the present invention is that these monoclonals, either separately or as a collection may be used directly to detect virus particles or antigens in clinical samples by the "immunodot" test or any similar modification relating to direct detection of viral antigens.

In summary: the present invention provides a method of preparing monoclonal antibodies reactive to immediate early and/or early HCMV antigens, such monoclonal antibodies per se, and their use in detecting HCMV; methods for detecting viral antigens, especially HCMV antigens, using monoclonal antibodies, and the use of monoclonal antibodies to distinguish between HCMV-specific IgM and HCMV-specific IgG.

The preparation of monoclonal antibodies is effected according to cell fusion technology known per se, in which myeloma cells are fused with spleen cells of mice which have been immunised with HCMV antigens. The type of monoclonal antibodies raised, and the spectrum of their reactivity against different HCMV antigens is determined by the nature of antigen preparation used to immunise mice. In the present specification, a variety of different antigen preparations derived by extraction of HCMV infected human cell extracts at different stages of infection and by different extraction techniques were used to derive a variety of monoclonal antibodies reactive against different HCMV antigens.

The following examples illustrate the invention.

MANUFACTURE OF THE MONOCLONAL ANTIBODIES (a) Antigen preparation

Laboratory strains of HCMV AD169 and Davis were grown in tissue culture of human embryo fibroblasts (HEF). The viruses were harvested when complete cytopathic effect was observed. This took 8–10 days post-infection (p.i.). After clarification of cellular debris from the supernatants at 2,000 rpm for 10 min, the virus was pelleted at 25,000 rpm (T35 fixed angle rotor) for 3 hours or at 35,000 rpm for 2 hours. The concentrated virus was partially purified between 70% and 20% sucrose cushions. The cushion layering was done at 28,000 rpm (SW 28.1 rotor) for 3 hours. The virus band layered onto 70% sucrose cushion was dialysed against phosphate buffered saline (PBS, pH 7.2, 0.01M) and the amount of protein is determined by reading the absorbance at 280 nm. Amount of protein was about 670 ug/ml from $2 \times 175$ cm$^2$ flasks of Davis infected HEF cells. The samples were allowed to retain their infectivity. The reasoning for the latter is the allowance of the induction of immediate early and early antigens of HCMV in the mouse cells in vivo.

(b) Immunisation of mice

Fifteen eight week old Balb/c/J female mice were immunised with sucrose cushion purified HCMV antigens. Single intraperitoneal injection is given using HCMV proteins without and with incomplete Freund's adjuvant in a form of a stable emulsion. The protein concentration varies from 45 ug to 165 ug and is indicated in Table 1. Mice were test bled from the tail vein on days 20–23 post-immunisation. The mouse sera were tested by indirect immunofluorescence at 1/40 dilutions against a range of HCMV antigens immediate early ($\alpha$), early ($\beta$) and late ($\gamma$).

The HCMV antigens were blocked with undiluted rabbit serum to eliminate non-specific binding through Fc receptors induced by HCMV strains. The reactivity in mouse sera was detected with anti-mouse IgG fluorescein isothiocyanate (FITC) conjugates at a predetermined dilution specific to each batch of conjugates.

More detailed description of immunising antigens and the results of mice pre-selection is given in Table 1. These mice were finally used in the cell fusions. All mice selected showed a preferential response to HCMV (AD 169 or Davis) infected cells compared to uninfected cellular antigens at this stage. Seventy-one to 198 days (Table 1) after the first injection the mice were boosted with twice the amount of protein/mouse. No adjuvant was used for this second inoculation. Four days after the booster mice were killed and the spleen was removed for the preparation of the monoclonal antibodies.

(c) Cell cultures and cell fusions

The following materials and media were used. RPMI 1640 was obtainable from Flow. It was made up freshly with sodium pyruvate (1.8 mM), glutamine (2.0 mM), penicillin (100 units/ml) and streptomycin (100 ug/ml). Complete HAT medium consists thus, completed RMPI 1640 as well as hypoxanthine ($10^{-4}$M), aminopterin ($4 \times 10^{-7}$M), thymidine ($1.5 \times 10^{-5}$M) and 10% foetal calf serum (FCS). A 50% (w/v) solution of polyethyleneglycol 4,000 (PEG 4,000, Merck) in RPMI 1640 was prepared.

The fusion with an azaguanine-resistant P3×63.Ag8/NS-1, HAT medium sensitive cell line was carried out with small modifications according to the methods described by Fazekas de St. Groth and Scheidigger, J. Immunol. methods, 35, 1–25 (1980). The spleen cells were harvested by pressing splenocytes through a wire mesh into serum-free RPMI 1640 medium. Myeloma cells were harvested at an exponential phase of their growth ($10^5$–$10^6$ cells/ml) and the growth medium removed. They were then suspended at the ratios listed in Table 2 (i.e., fusion A ratio was made up from $7.2 \times 10^7$ splenocytes and $10^7$ P3×63.Ag8/NS-1 myeloma cell line) and sedimented in 20 ml of serum-free medium in a 30 ml conical universal container. 200×g for 15 min to pellet all the cells.

To the completely drained cell sediment was added dropwise 1.0 ml of 50% PEG 4,000 solution over a period of 60 s. Another 60 s was used for an incubation at 37° C. and a gentle dispersion of cells. 10 ml of serum-free RMPI 1640 were added with gentle shaking during 4–5 minutes.

The mixture of cells was pelleted and serum-free medium was replaced by 10 ml of medium supplemented with 10% FCS. 10 ml of normal splenocytes from 1 mouse were added as feeder cells. The cells were left at 37° C. for 1 hour. This medium was replaced with 60 ml of complete HAT medium and then placed in six 96 well plates (100 ug/well). The cultures were fed twice a week by initially adding 100 ul of complete HAT medium and then replacing half of the medium with fresh HAT medium.

(d) Detection of CMV-specific hybridomas by immunofluorescence

A standard indirect immunofluorescence technique was adopted using CMV-infected HEF at various times post-infection (p.i.).

The HCMV cells were scraped with 3–4 mm glass balls at 14 hours p.i. after 12 hours of 100 ug/ml cycloheximide and 2 hours release of the block for immediate early antigens ($\alpha$) and 24 hours of 40 ug/ml phosphonoformic acid block for early antigens ($\beta$) and at 5 days p.i. for late HCMV antigens ($\gamma$).

$3 \times 10^4$ cells/spot were air dried and fixed in cold acetone. The slides were stored at $-20°$ C. with silica gel for continuous use. The HCMV infected cells were blocked with undiluted rabbit serum to block the non-specific Fc-receptor binding. Supernatants from all hybrids were scored for the reaction with infected and uninfected cells. This is monitored with anti-mouse IgG FITC conjugate and microscope with UV attachments. Anti-mouse IgG FITC was required not to cross-react with rabbit or foetal calf sera.

(e) Detection of CMV-specific hybridomas by ELISA

This method was adapted from Booth et al. (1979), J. Clin. Pathology, 32, 122–127. The glycine buffer (pH 9.6) infected cell extracts were titrated using CMV antibody positive human sera. The titrated dilution (usually 1/200–1/800) was then used to coat polyvinyl chloride plates in dicarbonate buffer pH 9.6 supplemented with 0.1% sodium azide for 16 hours at 4° C. The remaining binding sites were blocked with 3% ovalbumin solution in phosphate buffer saline (PBS pH 7.2) for 2 hours at 20° C. Neat hybridoma culture supernatants were reacted with HCMV antigen and the mouse antibody binding was detected with anti-mouse IgG alkaline phosphatase (AP) conjugate. The plates were washed five times with PBS+0.1% Tween 80. The conversion of AP substrate was monitored at 405 nm.

In the following further description reference will be made to the accompanying drawings in which:

FIG. 1 gives the result of an ELISA assay of Davis CMV extract antigen dilutions with different monoclonal antibodies;

RESULTS (a) Initial Screening by immunofluorescence

Initially five mice were selected to use their spleens in fusions with mouse myeloma cell line. Table 1 illustrates the antibody response in these mice. They all showed more reactivity with viral polypeptides compared to cellular antigens prior to fusion.

Of the 2886 possible culture wells, 1290 showed growth of hybridomas. The supernatants were tested for HCMV specific antibodies in the indirect immunofluorescence test. With the range of HCMV antigens 94 showed high binding to CMV infected cells and a negative or slight cross-reactivity with uninfected cells. The pattern of immunofluorescence ranged from nuclear, to cytoplasmic or mixed. They all reacted with late HCMV antigens. Four of these hybridoma supernatants also showed reactivity with immediate early and early CMV antigens. The designation of all is HCMV-15, HCMV-16, HCMV-17 etc., to HCMV-100.

(b) Initial screening by ELISA

Figure 1:
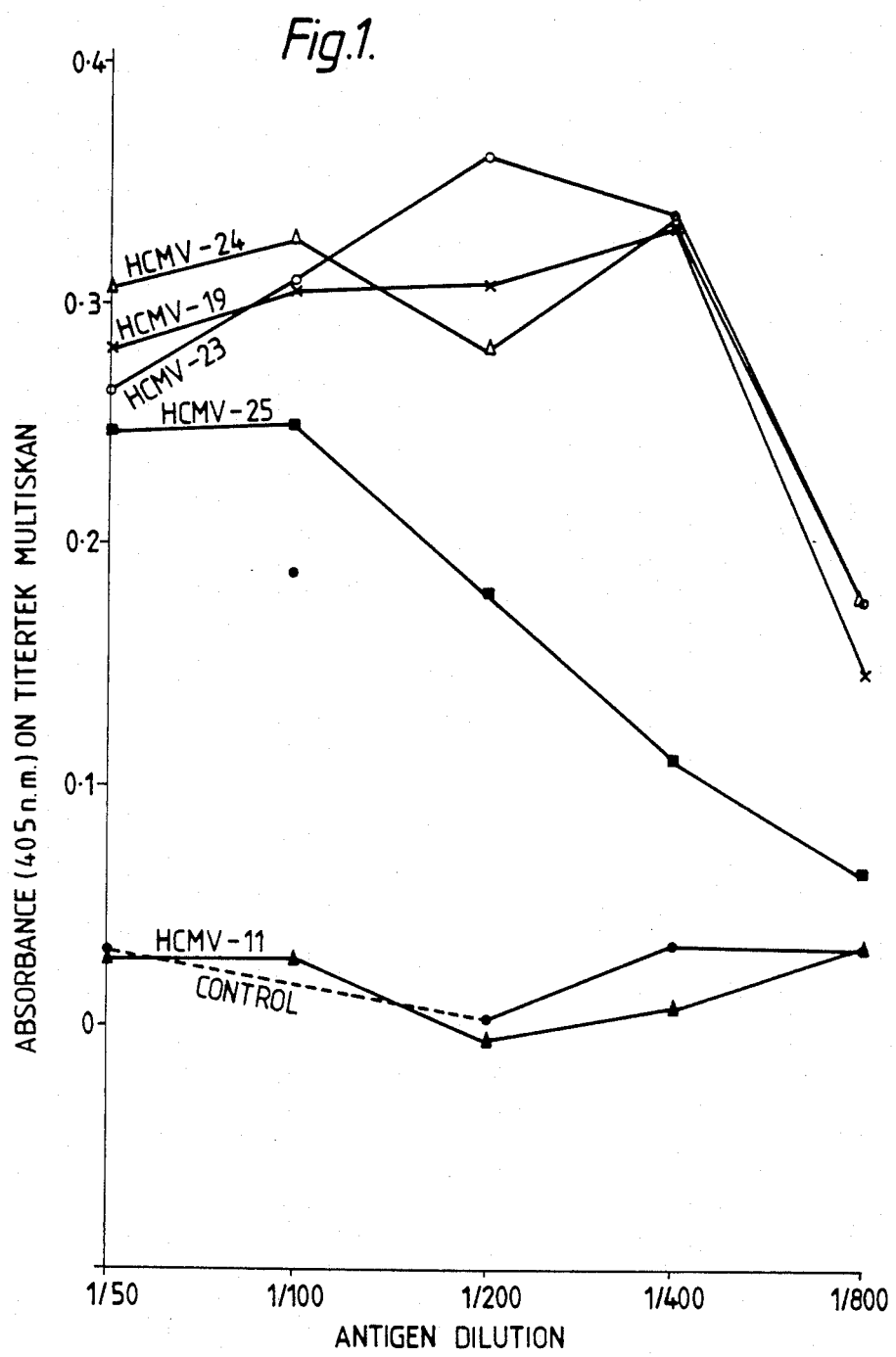

The same supernatants were also tested by ELISA test. Considerably fewer in number showed distinct reactivity with ELISA antigens. Four of these showed consistently high reactivity with the ELISA antigen extracts. For the purpose of this invention the reactivity of these four hydridoma supernatants is illustrated in FIG. 1. Other hybridoma supernatants showed a lower range of reactivity. This lower range also selected additional 5 hybridomas not positive by immunofluorescence. This brought the total of HCMV reactive mouse hybridoma supernatants to 99 from 1290 growing hybrids (Table 2).

(c) Cloning and stabilisation of HCMV-specific antibodies

For the preparation of stable hybridoma lines, all 99 HCMV specific hybridomas were expanded from their 96 well plates to 2×1 ml cultures in 24 well plates (Costar). Eighty-five/99 specific cultures grew and were placed in liquid nitrogen storage at this stage. Forty-nine HCMV specific hybridomas were cloned successfully by limiting dilution in microtitre plates with mouse splenocytes as the feeder layer. The cloning was begun at the point of expansion to 2×1 ml 24 cultures and was repeated if necessary directly with hybridomas stored in liquid nitrogen. An example of the results of cloning of the hybridomas is given in Table 3. These hybridomas were selected randomly to illustrate the procedure of cloning. All other clones were cloned in a similar fashion. The summary of results for 86 selected hybridomas, based mainly on immunofluorescence, is given in Table 4. From each hybridoma two to four strongly positive cultures were expanded for both ascites production and storage. In all cases the subsequent clones were treated individually when stored in liquid nitrogen. The new nomenclature however does not distinguish between such sub-clones.

(d) Isotypes of immunoglobulin

Hybridoma supernatants were concentrated 20× using Amicon protein concentrators. These were reached with a panel of chain specific anti-mouse Ig reagents (Miles Lab. Ltd.) to form a precipitin line in an Ouchterlony test.

This batch of rabbit sera specific for $\gamma_{2a}$ and $\gamma_{2b}$ chains show a great reaction in their performing in this system. An additional technique was therefore used for additional confidence. Microtitre polyvinyl chloride plates were coated with rabbit chain specific polyclonal anti-mouse immunoglobulin reagent at 1/1000 dilution. The plates were then blocked with 3% ovalbumin solution in PBS and the polyclonal reagents was reacted with hybridoma supernatants which were not concentrated. After washing five times with PBS+0.1% Tween 80 the mouse immunoglobulin bound was detected with a general anti-mouse immunoglobulin labelled with alkaline phosphatase (Miles Lab. Ltd.)

Examples of isotypes and chain characterisation were given in Table 5.

(e) Evaluation of specificity of binding to HCMV proteins

Figure 2:
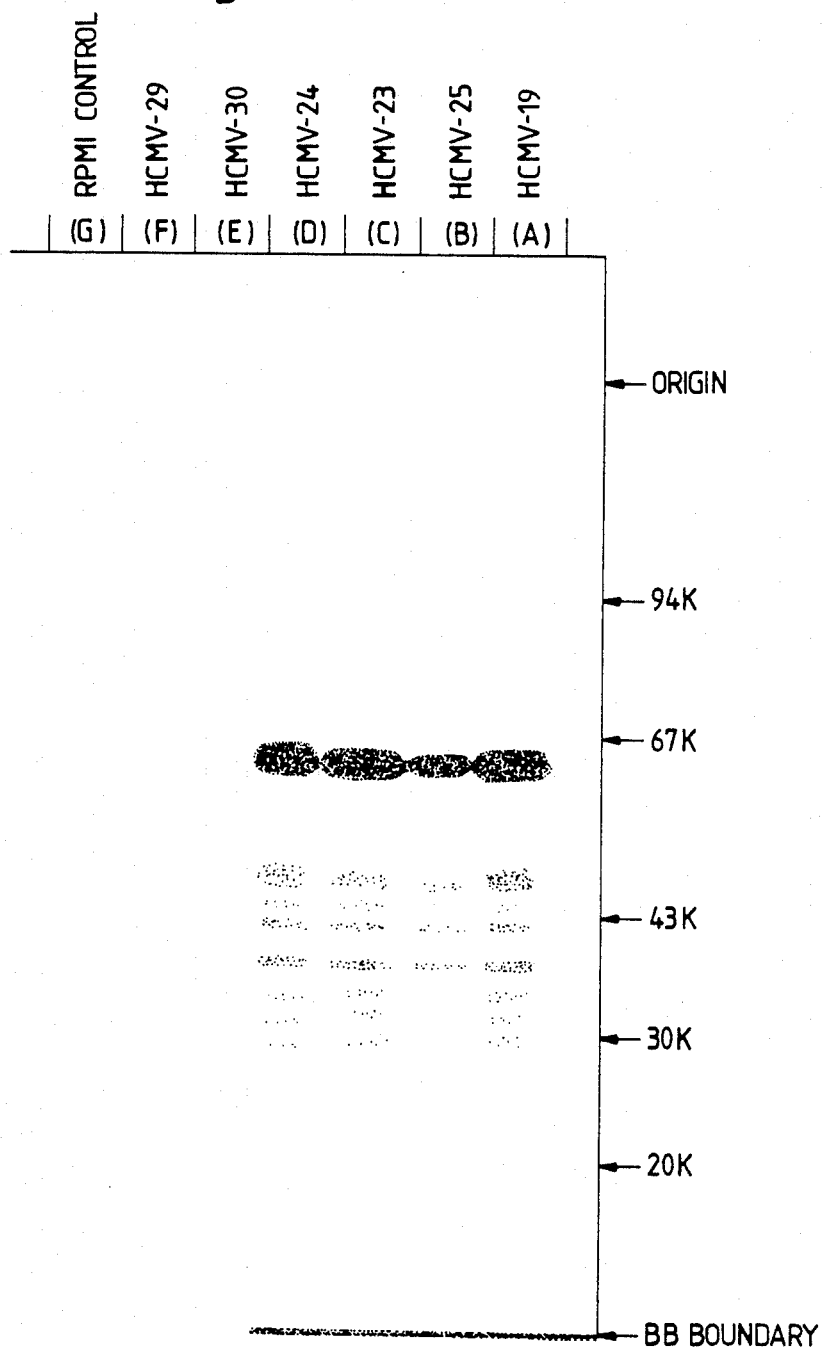
FIG. 2 shows the immunoprecipitation of $^{35}$S-methionine labelled NT buffer extracts of AD169 infected HEF cells with HCMV monoclonal antibodies.

HEF cells were infected with AD-169 virus at 5 p.f.u./cell in 75 cm$^2$ plastic flask (Nunc). After 5 days the infected and control cells were exposed to 50 uCi/ml of $^{35}$S-methionine (800 mCi/mmol; Amersham) in medium containing 1/5th of the concentration of unlabelled methionine. After 24 h labelled cells were washed three times with Tris-buffered saline (0.1M pH 7.4) and solubilised in 1 ml of (1) TT buffer (1% Triton X-100, 0.1% SDS, 50 mM Tris, 150 mM NaCl1, 100 KIU aprotinin, pH 7.2) and in (2) NT buffer (1% Nonidet P40, 40 mM Tris, 0.6M NaCl, 2% glycerol, 2 mM CaCl$_2$, 1 mM MgCl$_2$, 4 mM EDTA, pH 9.0 (Blanton and Tevethia, 1981) for 20 min. The cells were sonicated for 30 s and centrifuged at 30,000 rpm for 1 h in Beckman SW50 rotor. 600,000 cpm of the solubilised cellular antigens were mixed with 0.5 ml samples of monoclonal antibodies (tissue culture supernatants) and the mixtures were incubated at 40° C. overnight. 1/200 dilution of anti-mouse IgG (Dakopatts) aids immune precipitation. The precipitates were collected with 5 mg of Protein A-Sepharose (Pharmacia, Sweden) and pellets were washed extensively in (1) TT buffer three times, TBS once and TB (pH 7.2) once or (2) with NT washing buffer (1% Nonidet P40, 40 mM Tris, 0.5M LiCl, 0.1M NaCl, pH 7.2) three times, TBS and TB once. The pellets were then heated at 85° C. for 5 min in electrophoresis sample buffer and analysed by SDS-polyacrylamide slab-gel electrophoresis (Laemmli, 1970), Protein markers were phosphorylase B 94,000; bovine serum albumin 67,000; soybean trypsin inhibitor 20,100) (Pharmacia, Sweden). Gels were stained with 0.25% Coomassie blue to visualise the markers and destained (25% methanol, 5% acetic acid) prior to fluorography. Fluorography was carried out using 20% PPO (2,5-diphenyloxazole) in dimethylsulphoxide (Bonner and Laskey, 1974; Laskey and Mills, 1975) prior to the exposure to X-ray film (Kodak X-mat AR film).

some of the results of these immunoprecipitations are illustrated in Table 6 and FIG. 2. Strong binding was seen with a group of monoclonal antibodies with a 66K major polypeptide.

The examples shown in the FIG. 2 includes HCMV-19, HCMV-23, HCMV-24, HCMV-25 (tracks a, b, c, d) monoclonal antibodies which react preferentially with the 66K peptide thought to be matrix HCMV major peptide. Other HCMV peptides were brought down in the immunoprecipitates (Table 6). This contrast with another major group of monoclonal antibodies illustrated by HCMV-29 monoclonal (track f) showing a weaker but completely different pattern. Control (track g) using RPMI 1640 medium and identical number of counts extracted from HCMV infected cells did not bring down any HCMV polypeptides. Control uninfected cells also did not react with these monoclonal antibodies (not illustrated). This confirms their specificity for HCMV specific polypeptides.

The complexity of the pattern of monoclonal antibodies HCMV-19, HCMV-23, HCMV-24 and HCMV-25 (tracks a, b, c, d) was being investigated further. Immunoprecipitation or immunoaffinity chromatography with these monoclonals appears to yield a large number of viral components. The property was associated with the primary reactivity of these monoclonal antibodies with 66K matrix protein and was specific for this group.

HCMV-29 or HCMV-31 in contrast brought down a small number of polypeptides (Table 6) from the same extract preparation.

(f) Evaluation of timing of appearance of HCMV antigens detected by monoclonal antibodies The individual antibody collection was tested in reactivity with HCMV antigens induced at various times post-infection (p.i.) using chemical blocks described in detection of HCMV antigens by immunofluorescence. One example of various cross-reactivities is given in Table 7. HCMV-19, HCMV-23 and HCMV-24 were shown to react with immediate early ($\alpha$), early ($\beta$) and late ($\gamma$) antigens and two HCMV strains AD169 and Davis, while others (HCMV-39) showed no immunofluorescence with $\alpha$ and $\beta$ antigens and react specifically with $\gamma$ antigens of AD169 only.

HCMV-19, HCMV-23 and HCMV-24 monoclonal cocktail was proving useful in detection of antigens of clinical isolates. Seventeen clinical samples of urine or throat swabs were passed in HEF cells and fixed at 24 h. The appearance of positive nuclear immunofluorescence in six of the samples correlates with positivity as determined by classical diagnostic virology isolations of HCMV (Table 8).

The monoclonal cocktail HCMV-19, HCMV-23 and HCMV-24 was also used in rapid titration techniques of all HCMV strains and in estimation of the reduction of HCMV infectivity (i.e. neutralisation or anti-viral drugs).

In addition to monoclonal antibodies which can detect an antigen present throughout the viral cycle of a wide range of HCMV isolates, the collection was also illustrating the capability of distinguishing AD169 and Davis strains (HCMV-27, HCMV-34 and HCMV-39) and is beginning to be useful in distinguishing over strains of HCMVs (Table 7).

(g) Antigen capture assay

Figure 4:
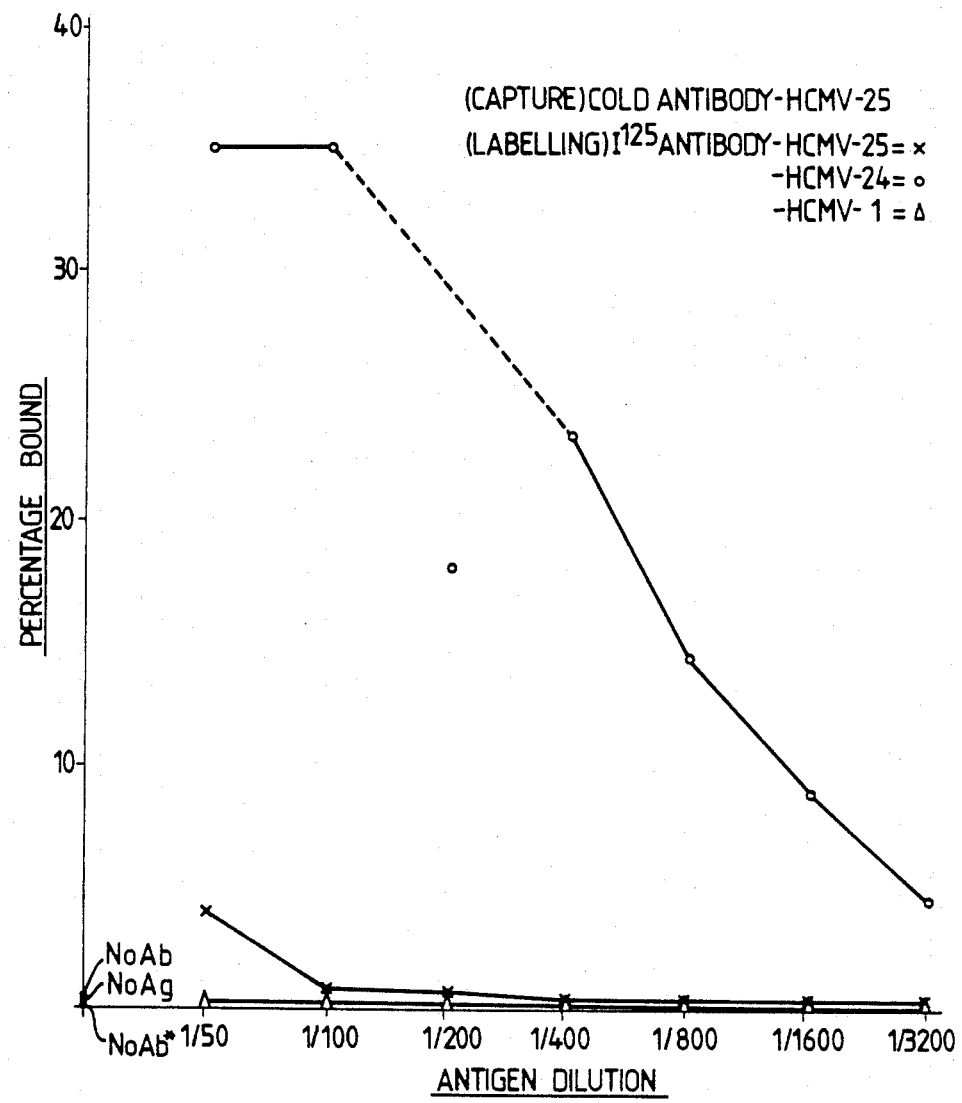
Figure 5:
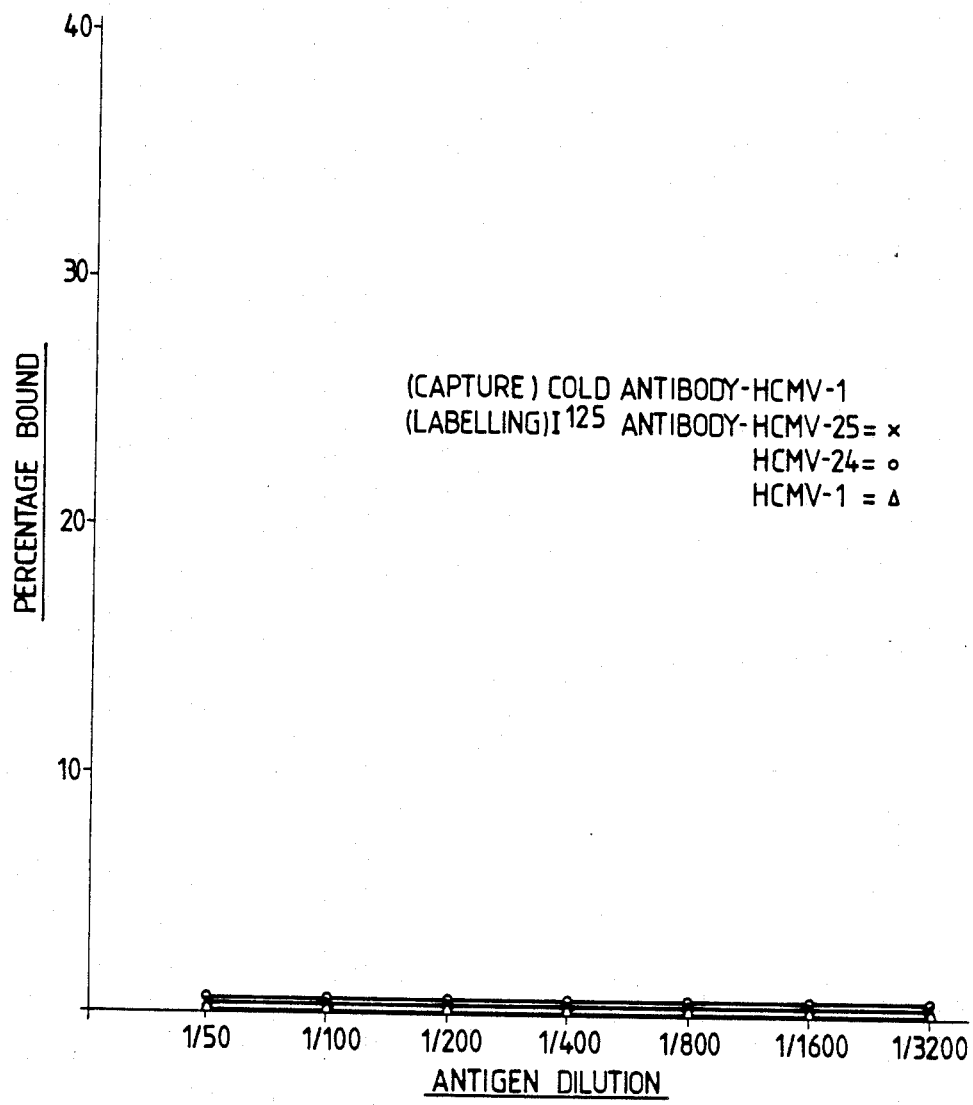

We we interested in confirming that HCMV-24 and HCMV-25 monoclonal antibodies detect the same antigen and if so do they react with different epitopes. This was achieved by coating polyvinyl plates with HCMV-24 (FIG. 3) and with HCMV-25 (FIG. 4). The control plate was coated with HCMV-1 (FIG. 5) known to react with a different set of HCMV polypeptides (141K, 60K and 36K).

Figure 3:
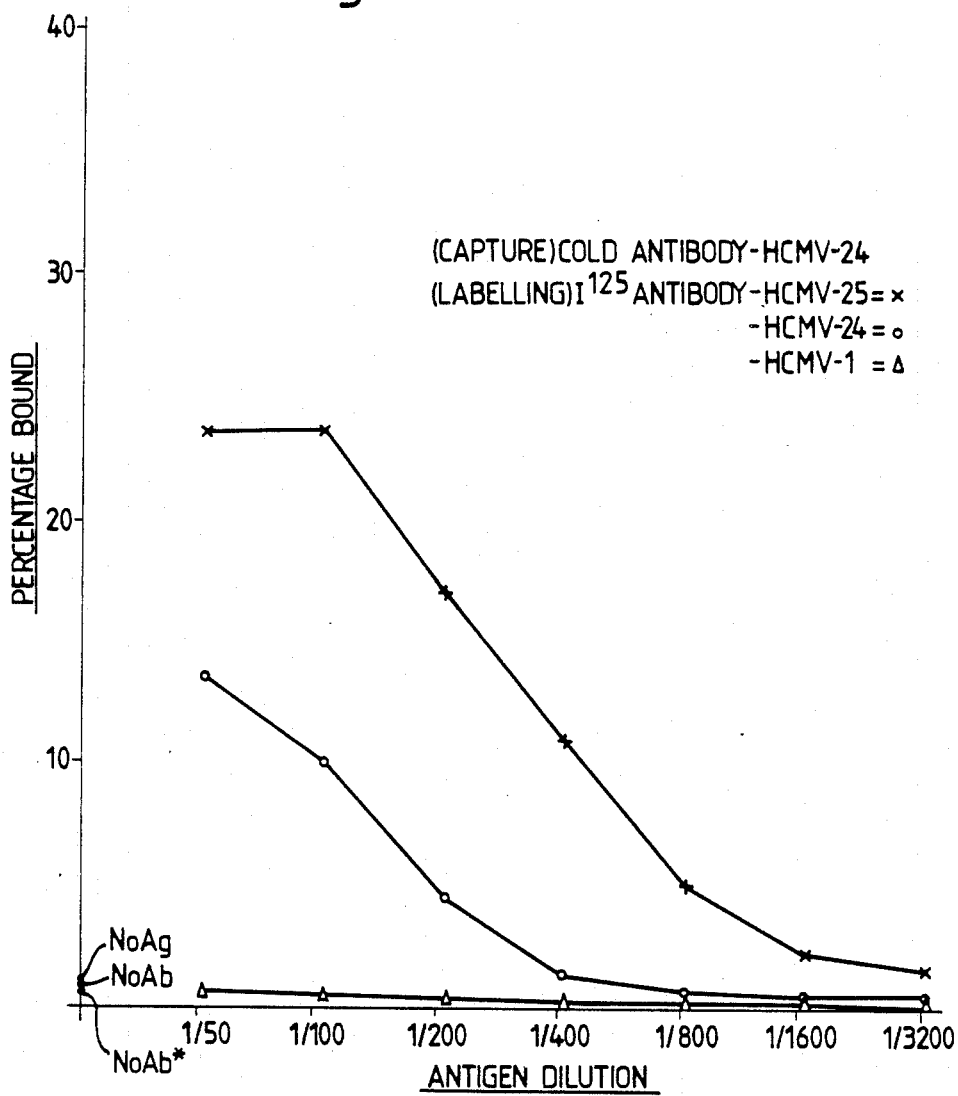
FIGS. 3 to 5 show the results of solid-phase sandwich assays using microtitre plates coated with different HCMV monoclonal antibodies respectively.

From FIG. 3 HCMV-25 MoAb binds to HCMV-24 captured antigen. This trend was reversed in FIG. 4, confirming the MoAbs HCMV-24 and HCMV-25 reacted with same antigen but different epitopes. For the purposes of direct rapid diagnostic techniques we have coated polystyrene beads (6 mm, Northumbria Limited) with HCMV-25 monoclonal. This was used in capture of laboratory strain AD169 antigens in urine samples and on a collection of clinical specimens. The capture of CMV antigens was detected with HCMV-24 monoclonal (Table 9).

(h) IgM assay (Antibody capture assay)

The MoAb HCMV-24 and HCMV-25 were used as a last detection system in a IgM-antibody capture radioimmunoassay (MACRIA) modified from the description of Sutherland and Briggs (1983) J. Med. Virology, 11, 147–159. Briefly, microtitre plates or polystyrene beads (Northumbria Ltd.) were coated with anti-human IgM antibody (Seward 1/200–1/400 dilution) to capture specifically IgM. This was allowed to react with glycine buffer extracted HCMV antigen (1/10–1/40 dilution). This reaction was detected with the specific HCMV MoAb. It was clear from binding to antigen captured (1/40 dilution) by HCMV IgM positive human sera (HS (1)+(4)) that MoAb's work singly but benefit from being used as a mixture (Table 10). The cocktail HCMV-24, HCMV-25 and HCMV-1 shows high ratio compared to the same cpm of single MoAb. Two human CMV IgM negative sera (HS (2)+(3)) were also found negative by this test.

The collection of human sera using the above cocktail was extended to 17 sera (Table 11).

Positive/negative antigen ratios and differentials were used. The overall increase in ratios was due to a higher concentration of HCMV antigen (1/10) used in this set of experiments. The group of unknown human sera can be more clearly distinguished by basing the judgement both on the ratios and differentials, following the pattern of the known samples.

(i) Immunodot assay

The immunodot technique is based on non-specific protein binding to nitrocellulose membranes using Hybridot filtration apparatus. This allowed handling of 96 samples simultaneously. Test urine samples (up to 1 ml. in volume) were trapped, air dried for 2–3 hours, and the membranes blocked with 3% ovalbumin solution. Specific monoclonal HCMV antibodies were allowed to react with the protein dots. The binding of monoclonal antibodies was detected with anti-mouse immunoglobulin labelled with immunoperoxidase. (Bio-Rad or Inveresk Research International.) The enzyme reactivity was detected with 3-amino-9-ethylcarbazole; and specific reaction appears as a brown coloured dot.

Figure 6:
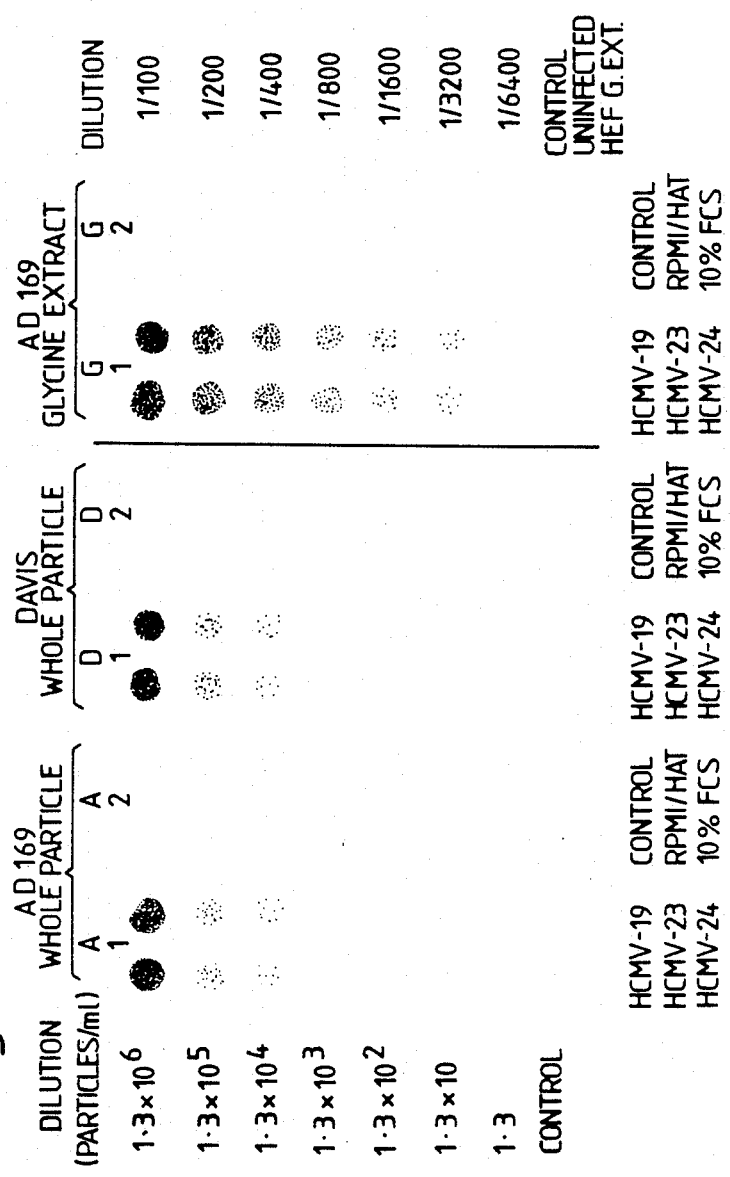
FIG. 6 illustrates the reactivity of a cocktail of HCMV antibodies with AD169 and Davis virus particles and AD169 glycine extracts in an immunodot system.

The potential of the HCMV MoAb collection is illustrated in an immunodot assay using whole viral particles as well as glycine buffer (pH 9.6) extracts of infected cells (FIG. 6). A cocktail of HCMV-19, HCMV-23 and HCMV-24 reacted with both. Control RPMI 1640 medium was negative. MoAb cocktail can detect down to $10^4$ particles/dot and should be useful in a direct evaluation of clinical samples for the presence of HCMV antigens.

Non-specific immunoperoxidase activity was seen in some normal urine samples which was linked to the use of anti-mouse IgG IP. It was destroyed with 2% SDS pretreatment of urine samples which retained some CMV monoclonal antibody activity. With such pretreatment the monoclonal antibodies used have to be positive in Western transfer (Towbin et al, Proc. Natl. Acad. Sci., USA, 76, 4350–4355, 1979) for these to work in immunodot. (In the Western transfer, antigen protein is treated with reducing agent and SDS-PAGE transferred to a nitrocellulose membrane, and reacted with antibodies. These antibodies which react are recognising the primary amino-acid structure, and hence can be used for the pretreated samples herein.) HCMV-25 and HCMV-1, for example, were found to be suitable.

Using these conditions to remove the false positives, experiments continued with the immunodot detection technique by evaluating 21 urine specimens blind. 14 from these were positive by tissue culture isolations. Immunodot detected 7/14 positive and gave no false positive results. (Table 12). A tendency to miss positive specimens was shown more frequently with specimens with longer delay in tissue culture isolations. For positives detected, the average isolation time was $8.2 \pm 4$ days and for positives missed by the immunodot, the isolation time was $17.4 \pm 4.8$ days in tissue culture. The detection time in tissue culture will be a measure of number of infectious particles/HCMV antigen present in urine. This indicates that the immunodot test as described is not currently sensitive enough to detect low clinical levels of HCMV. However, sensitivity can be increased by, for example, amplification techniques now known (see for example EP 49606A, EP 27036A, EP 58539A and WO 81/00725).

TABLE 1

| | | SUMMARY OF HCMV MONOCLONAL ANTIBODY FUSIONS | | | | | | |
|---|---|---|---|---|---|---|---|---|
| Mice No. | Fusion No. | Antigen | Protein conc./mouse 1st inoc. | IF test (day 21–23) | | | Protein conc. booster | Post-immun. booster (days) |
| | | | | Davis | AD169 | C | | |
| 1 | 4 | AD169 | 133 μg | ± | ++ | ± | 260 μg | 198 |
| 2 | 5 | AD169 | 165 μg | ++ | +++ | + | 330 μg | 71 |

TABLE 1-continued

| | | | | | | | | | | |
|---|---|---|---|---|---|---|---|---|---|---|
| 3 | 7 | Davis IFA | 133 μg | ++++ | +++ | + | 260 μg | 71 |
| 4 | A | Davis IFA | 133 μg | ++++ | +++ | ++ | 260 μg | 146 |
| 5 | B | AD169 (1d,p.i.HSA) | 51 μg | +(IE+) | ++(IE++) | − | 100 μg | 108 |
| 6 | C | AD169 (3d,p.i.HSA) | 45 μg | +++(IE+) | +++(IE±) | − | * | * |

KEY: 
IFA = incomplete Freund's adjuvant
IE = immediate early CMV antigens
HSA = high salt buffer extracted antigen
+
++
+++   } = increasing intensity of immunofluorescence
++++
Davis & AD169 = HCMV laboratory strains
C = control uninfected cells
* = not tested
− = negative TABLE 2
THE RATE OF HCMV SPECIFIC HYBRIDOMA FROM MOUSE SPLENOCYTES FUSIONS WITH NS-1

| Mouse No. | Fusion No. | Ratio mouse splenocytes: NS-1 cells | HCMV specific clones/ total hybrids |
|---|---|---|---|
| 1 | 4 | 8.4:1 | 1/450 |
| 2 | 5 | 10:1 | 24/300 |
| 3 | 7 | 10:1 | 0/36 |
| 4 | A | 7.2:1 | 74/384 |
| 5 | B | 9:1 | 0/120 |
| 6 | C | * | * |

TABLE 3
AN EXAMPLE OF CLONING DATA

| Culture | No. of growing clones/well | No. tested | No. positive |
|---|---|---|---|
| HCMV-16 | 13 | 6 | 2 |
| HCMV-19 | 4 | 4 | 0 |
| HCMV-19 | 104 | 24 | 4 |
| HCMV-20 | 31 | 31 | 25 |
| HCMV-26 | 12 | 7 | 7 |
| HCMV-27 | 23 | 6 | 5 |
| HCMV-27 | 23 | 6 | 5 |
| HCMV-29 | 7 | 6 | 6 |
| HCMV-30 | 25 | 6 | 6 |
| HCMV-32 | 18 | 6 | 6 |
| HCMV-33 | 30 | 6 | 1 |
| HCMV-34 | 23 | 6 | 2 |

TABLE 4
SUMMARY OF GROWTH AND CLONING OF HCMV SPECIFIC ANTIBODIES FUSION 4, FUSON 5 and FUSION A

| Initially selected clones | ELISA at 405 mm | IF CMV AD169 | C | Ist Cloning | IF CMV AD169 | C | New Nomenclature |
|---|---|---|---|---|---|---|---|
| 43A1 | | + | − | 43A1-1 | + | − | HCMV-15 |
| 51C1 | | ++ | ± | 51C1-1 | +++ | − | HCMV-16 |
| | | | | 51C1-2 | ++++ | − | |
| 51C10 | | ++ | − | 51C10-1 | + | − | HCMV-17 |
| | | | | 51C10-2 | + | − | |
| 51C11 | | ++ | − | 51C11-1 | +++ | − | HCMV-18 |
| | | | | 51C11-2 | +++ | − | |
| 53G5 | | +++ | − | 53G5-1 | +++ | − | HCMV-19 |
| | | | | 53G5-2 | +++ | − | |
| 54A4 | | ++ | − | 54A4-1 | +++ | − | HCMV-20 |
| | | | | 54A4-2 | +++ | − | |
| 54C3 | | +++ | − | 54C3-1 | +++ | − | HCMV-21 |
| 54D3 | | ++++ | − | 54D3-1 | +++ | − | HCMV-22 |
| 54D6 | | +++ | − | 54D6-1 | ++++ | + | HCMV-23 |
| | | | | 54D6-2 | +++ | ± | |
| 54E4 | | +++ | − | 54E4-1 | +++ | ± | HCMV-24 |
| | | | | 54E4-2 | +++ | ± | |
| 54H1 | | +++ | − | 54H1-1 | ++++ | ± | HCMV-25 |
| 55C8 | | ++ | − | 55C8-1 | + | − | HCMV-26 |
| | | | | 55C8-2 | +++ | − | |
| | | | | 55C8-3 | +++ | ± | |
| 55D10 | | +++ | − | 55D10-1 | +++ | − | HCMV-27 |
| | | | | 55D10-2 | +++ | − | |
| 55E8 | | +++ | − | 55E8-1 | +++ | − | HCMV-28 |
| | | | | 55E8-2 | ± | | |
| 56A1 | | +++ | − | 56A1-1 | ++++ | − | HCMV-29 |
| | | | | 56A1-2 | ++++ | − | |
| 56B3 | | +++ | − | 56B3-1 | +++ | − | HCMV-30 |
| | | | | 56B3-2 | ++ | − | |
| | | | | (56B3-2) | +++ | − | |
| 56B4 | | +++ | − | 56B4-1 | +++ | − | HCMV-31 |
| 56B6 | | +++ | − | 56B6-1 | +++ | − | HCMV-32 |
| | | | | 56B6-2 | +++ | − | |
| 56C2 | | + | − | 56C2-1 | +++ | − | HCMV-33 |
| 56E3 | | +++ | − | 56E3-1 | + | − | HCMV-36 |
| | | | | 56E3-2 | +++ | − | |
| (56C3) | | | | (56C3-2) | (+++) | | |
| 56C5 | | +++ | − | 56C5-1 | +++ | − | HCMV-34 |

TABLE 4-continued
SUMMARY OF GROWTH AND CLONING OF HCMV SPECIFIC ANTIBODIES
FUSION 4, FUSION 5 and FUSION A

| Initially selected clones | ELISA at 405 mm | IF CMV AD169 | C | Ist Cloning | IF CMV AD169 | C | New Nomenclature |
|---|---|---|---|---|---|---|---|
| | | | | 56C3-2 | +++ | − | |
| 56E1 | | +++ | − | 56E1-1 | | | HCMV-35 |
| 56G8 | | +++ | − | 56G8-1 | +++ | − | HCMV-37 |
| 56H5 | | +++ | − | 56H5-1 | +++ | − | HCMV-38 |
| | | | | 56H5-2 | +++ | − | |
| 56H6 | | ++++ | − | 56H6-1 | +++ | − | HCMV-39 |
| | | | | 56H6-2 | +++ | − | |
| A1H12 | 0.109 | ± | ± | | | | HCMV-40 |
| A2A2 (A2H2) | | +++ | + | A2A2-1 | ++ | − | HCMV-41 |
| | | | | A2A2-2 | +++ | − | |
| A2A5 | | +++ | ± | A2A5-1 | ++ | − | HCMV-42 |
| | | | | A2A5-2 | +++ | − | |
| A2A6 | | +++ | ± | | | | HCMV-43 |
| A2A8 | | +++ | − | A2A8-1 | +++ | − | HCMV-44 |
| | | | | A2A8-2 | ++ | − | |
| A2A10 | | ++ | − | | | | HCMV-45 |
| A2A11 | | ++++ | − | | | | HCMV-46 |
| A2C6 | 0.282 | + | − | | | | HCMV-47 |
| A2C7 | | ++ | − | A2C7-1 | ± | − | HCMV-48 |
| | | | | A2C7-2 | ± | − | |
| A2D4 | | ++++ | + | | | | HCMV-49 |
| A2F5 | | ++++ | − | A2F5-1 | + | − | HCMV-50 |
| | | | | A2F5-2 | ++ | − | |
| A2G1 | 0.117 | + | − | | | | HCMV-51 |
| A2G2 | 0.290 | +++ | − | | | | HCMV-52 |
| A2G4 | | ++++ | − | | | | HCMV-53 |
| A2G7 | | +++ | − | A2G7-1 | +++ | ± | HCMV-54 |
| | | | | A2G7-2 | +++ | − | |
| A2H3 | 0.144 | − | − | | | | HCMV-55 |
| A2H6 | | +++ | − | | | | HCMV-56 |
| A2H7 | | ++++ | − | A2H7-1 | +++ | − | HCMV-57 |
| | | | | A2H7-2 | ++ | − | |
| A3A1 | 0.069 | ++ | − | | | | HCMV-58 |
| A3A2 | | ++ | + | | | | HCMV-59 |
| A3A8 | | +++ | − | | | | HCMV-60 |
| A3A9 | | ++ | − | A3A9-1 | + | − | HCMV-61 |
| A3B3 | 0.093 | − | * | | | | HCMV-62 |
| A3C1 | 0.144 | − | * | | | | HCMV-63 |
| A3C2 | 0.096 | ± | * | | | | HCMV-64 |
| A3C6 | | +++ | | | | | HCMV-65 |
| A3D1 | | +++ | − | A3D1-1 | + | − | HCMV-66 |
| A3D5 | | ++ | + | A3D5-1 | ++ | − | HCMV-67 |
| | | | | A3D5-3 | ++ | − | |
| A3E7 | | +++ | − | A3E7-1 | + | − | HCMV-68 |
| | | | | A3E7-2 | + | − | |
| A3E9 | 0.353 | +++ | +++ | | | | HCMV-69 |
| A3F5 | | ++++ | +++ | A3F5-1 | ++ | − | HCMV-70 |
| A3F8 | | +++ | + | | | | HCMV-71 |
| A3F9 | | ++ | − | | | | HCMV-72 |
| A3G3 | | ++ | ± | A3G3-1 | +++ | − | HCMV-73 |
| | | | | A3G3-2 | +++ | − | |
| A3G10 | | ++ | − | | | | HCMV-74 |
| A3H1 | | + | − | A3H1-1 | ± | − | HCMV-75 |
| | | | | A3H1-2 | ++ | − | |
| A3H2 | | ++++ | ± | A3H2-1 | +++ | − | HCMV-76 |
| | | | | A3H2-2 | +++ | − | |
| | | | | A3H2-3 | +++ | − | |
| A4A6 | | + | − | | | | HCMV-77 |
| A4A7 | | +++ | − | | | | HCMV-78 |
| A4A9 | | +++ | + | | | | HCMV-79 |
| A4B3 | | +++ | − | A4B3-2 | +++ | − | HCMV-80 |
| A4C2 | | +++ | + | | | | HCMV-81 |
| A4C4 | | +++ | + | A4C4-1 | +++ | − | HCMV-82 |
| A4C9 | | +++ | + | | | | HCMV-83 |
| A4E10 | | +++ Nuclear | + | A4E10-2 | +++ | − | HCMV-84 |
| A4F10 | | ++ | + | | | | HCMV-85 |
| A4H2 | | ++++ | − | | | | HCMV-86 |
| A4H3 | | ++ | − | A4H3-1 | ++++ | − | HCMV-87 |
| | | | | A4H3-2 | ++++ | − | |
| A4H6 | | ++ | − | | | | HCMV-88 |
| A4H7 | | +++ | + | | | | HCMV-89 |
| A4H8 | | +++ | + | A4H8-1 | ++++ | − | HCMV-90 |
| | | | | A4H8-2 | ++++ | − | |
| | | | | A4H8-3 | ++++ | − | |
| | | | | A4H8-3 | ++++ | − | |

TABLE 4-continued
SUMMARY OF GROWTH AND CLONING OF HCMV SPECIFIC ANTIBODIES FUSION 4, FUSON 5 and FUSION A

| Initially selected clones | ELISA at 405 mm | IF CMV AD169 | C | 1st Cloning | IF CMV AD169 | C | New Nomenclature |
|---|---|---|---|---|---|---|---|
|  |  |  |  | A4H8-4 | ++++ | − |  |
| A5A5 | +++ | − |  |  |  |  | HCMV-91 |
| A5A6 | ++++ | + | A5A6-1 | ++++ | − | HCMV-92 |
|  |  |  | A5A6-2 | +++ | − |  |
| A5B2 | ++ | + |  |  |  | HCMV-93 |
| A5B10 | +++ | + | A5B10-1 | ++ | − | HCMV-94 |
| A5C3 | ++++ | − |  |  |  | HCMV-95 |
| A5D6 | +++ | − |  |  |  | HCMV-96 |
| A5E5 | +++ | + | A5E5-1 | ++ | − | HCMV-97 |
|  |  |  | A5E5-2 | + | − |  |
| A5H3 | +++ | ± |  |  |  | HCMV-98 |
| A5H11 | +++ | + | A5H11-1 | + | − | HCMV-99 |
| A5H12 | +++ | ± |  |  |  | HCMV-100 |

+, ++, +++, ++++ = Degrees of I.F.
IF = Immunofluorescence
C = Control

TABLE 5
ISOTYPES AND CHAINS OF A SAMPLE OF MoAb

| Monoclonal antibody | Isotype | Chains |
|---|---|---|
| HCMV-19 | IgG | $\gamma_{2a}$ |
| HCMV-17 | IgG | $\gamma_1$ |
| HCMV-21 | IgG | $\gamma_3$ |
| HCMV-35 | IgG | $\gamma_1$ |
| HCMV-40 | IgG | $\gamma_3$ |
| HCMV-54 | IgG | $\gamma_3$ |

TABLE 6
IMMUNE PRECIPITATION OF $^{35}$S—METHIONINE LABELLED AD169 INFECTED HEF CELLS, EXTRACTED WITH TT (NEUTRAL) AND NT (ALKALINE) BUFFERS WITH A SAMPLE OF MoAb

| Monoclonal antibodies | Polypeptides apparent molecular weights × $10^3$ Radioimmune precipitation | |
|---|---|---|
|  | TT buffer | NT buffer |
| HCMV-19 | * | (63), 56, 55, 48, 46, 43, 40, 39, 37, 36, 33, 31 |
| HCMV-23 | 66, 55 | (65), 56, 47, 44, 42, 39, 35, 32, 31 |
| HCMV-24 | 66, 55 | 126, (63), 57, 55, 47, 42, 39 |
| HCMV-25 | * | (65), 40 |
| HCMV-27 | * | 116, 100, 96, 93, 88, 883, 79, 75, 73, (67), 61, 57, 53, 51, 48, 44, 41, 40 |
| HCMV-29 | * | 96, 57 |
| HCMV-30 | * | 98, 56, 51 |
| HCMV-31 | * | 98, 56 |
| HCMV-33 | * | 123, 98, 96, 81, (65), 56, 51, 46, 42, 39, 37, 35, 31, 29 |
| HCMV-38 | * | 123, 98, 95, 81, (64), 56, 53, 47, 42, 39, 35, 31, 29 |
| HCMV-39 | * | 98, 56, 51 |

* = not tested
( ) = major band

TABLE 7
THE TIMING OF APPEARANCE OF HCMV ANTIGENS DETECTED BY HCMV MoAb IN AN INDIRECT IMMUNOFLUORESCENCE TEST

| Monoclonal Culture | 100 µg/ml Cycloheximide block | | 40 µg/ml phosphoroformic block | | 5 d p.i. | | 5 d p.i. |
|---|---|---|---|---|---|---|---|
|  | AD169 IE | Davis IE | AD169 E | Davis E | AD169 LA | Davis LA | AD169 LA |
| HCMV-19 | ++ | ++ | ++ | ++ | +++ | +++ | +++ |
| HCMV-23 | + | + | ++ | ++ | ++++ | +++ | ++ |
| HCMV-24 | ++ | + | ++ | +++ | +++ | +++ | +++ |
| HCMV-25 | − | − | + | + | ++ | ++ | + |
| HCMV-27 | − | − | ± | − | +++ | − | * |
| HCMV-34 | * | * | * | * | +++ |  |  |
| HCMV-36 | ± | − | − | + | +++ | − | * |
| HCMV-39 | − | − | − | − | ++++ | +++ | * |
| HCMV-29 | * | * | * | * | +++ | ++++ | * |

KEY
+, ++, +++, ++++ = increasing intensity of positive immunofluorescence staining
− = negative
± = negative, but some background
* = not tested

TABLE 8

INITIAL CLINICAL RESULTS WITH A POOL OF THREE MONOCLONAL HCMV ANTIBODIES (HCMV-19, HCMV-23, HCMV-24). URINE OR THROAT SWABS WERE TAKEN FROM BONE MARROW TRANSPLANT PATIENTS. ALL SAMPLES WERE INOCULATED INTO HUMAN EMBRYO FIBROBLASTS AND FIXED AT (a) 24 HOURS FOR INDIRECT IMMUNOFLUORESCENCE FOR EARLY ANTIGEN EA TEST, OR (b) OBSERVED FOR UP TO 30 DAYS FOR THE DEVELOPMENT OF CYTOPATHIC EFFECT.

|  | (a) EA test | (b) Conventional Culture |
|---|---|---|
| Number scored positive | 6 | 6 |
| Number scored negative | 11 | 11 |

TABLE 9

SPECIFIC CMV CAPTURE RADIOIMMUNOASSAY (RIA) WITH URINE SAMPLES, STORED −70° C.

| City Hospital Serum No. | Tissue culture isolation (No. days) | Date of RIA test | Average cpm | Ratio clinical sample/ negative control | IRI score (ratio >2.0) |
|---|---|---|---|---|---|
| 24095 | −* | 10.9.84 | 655 ± 78 | 2.25 | + |
| 24090 | − | 10.9.84 | 387 ± 14 | 1.33 | − |
| 23868 | − | 10.9.84 | 201 ± 3 | 0.69 | − |
| 25112 | − | 10.9.84 | 165 ± 38 | 0.63 | − |
| 24328 | +(24) | 10.9.84 | 206 ± 7 | 0.71 | − |
| 23931 | − | 10.8.84 | 306 ± 55 | 1.05 | − |
| 26997 | +(4) | 10.9.84 | 599 ± 113 | 2.06 | + |
| 24087 | − | 10.9.84 | 236 ± 19 | 0.81 | − |
| 24021 | − | 10.9.84 | 320 ± 42 | 1.10 | − |
| 23991 | +(11) | 10.9.84 | 270 ± 17 | 0.93 | − |
| 24334 | − | 10.9.84 | 233 ± 1 | 0.80 | − |
| 27257 | +(14) | 10.9.84 | 260 ± 18 | 0.89 | − |
| 33219 | −* | 24.9.84 | 889 ± 174 | 3.04# | + |
| 30113 | − | 24.9.84 | 309 ± 65 | 1.05# | − |
| 30130 | − | 24.9.84 | 324 ± 28 | 1.11# | − |
| 30380 | −* | 24.9.84 | 916 ± 186 | 3.13# | + |
| 09701 | − | 24.9.84 | 417 ± 125 | 1.42# | − |
| AD169/urine |  | 10.9.84 | 20333 ± 1627 |  |  |
| Urine |  | 10.9.84 | 292 ± 47 |  |  |

*negative by isolation but from previously positive patients, CMV IgM present in serum
ratio calculated using 10.9.84 control

TABLE 10

MACRIA WITH MONOCLONAL ANTIBODIES HCMV-24, HCMV-25 and HCMV-1

| Conjugate | HS1 | | HS2 | | HS3 | | HS4 | |
|---|---|---|---|---|---|---|---|---|
|  | CMV ratio | Control ratio | CMV ratio | Control ratio | CMV ratio | Control ratio | CMV ratio | Control ratio |
| HCMV-25 (57,000 cpm) | 2.72 | 1.06 | 0.72 | 1.06 | 1.00 | 1.06 | 1.40 | 1.06 |
| HCMV-24 (100,000 cpm) | 3.69 | 1.37 | 1.38 | 1.37 | 1.26 | 1.37 | 2.14 | 1.26 |
| HCMV-1 (80,000 cpm) | 3.34 | 1.55 | 1.13 | 1.55 | 1.43 | 1.55 | 2.01 | 1.43 |
| HCMV-24 HCMV-25 HCMV-1 (80,000 cpm) | 5.46 | 1.69 | 1.57 | 1.69 | 1.54 | 1.69 | 2.88 | 1.67 |
| HCMV-25 HCMV-1 74,000 cpm) | 3.38 | 1.29 | 1.21 | 1.29 | 1.06 | 1.29 | 2.50 | 1.27 |
| HCMV-24 HCMV-1 (75,000 cpm) | 5.31 | 1.30 | 1.38 | 1.30 | 1.30 | 1.30 | 2.61 | 1.30 |
| HCMV-24 HCMV-25 (85,000 cpm) | 4.36 | 1.25 | 1.44 | 1.25 | 1.08 | 1.25 | 2.13 | 1.25 |
| HCMV-24 HCMV-25 HCMV-1 (144,000 cpm) | 4.31 | 1.48 | 1.62 | 1.48 | 1.36 | 1.48 | 2.25 | 1.48 |

$$\text{CMV ratio} = \frac{\text{Davis CMV Ag in the presence of serum}}{\text{Control Ag in the presence of serum}}$$

TABLE 10-continued

Background ratio = Davis Ag in the absence of serum / Control Ag in the absence of serum ___ = significantly high CMV ratio

| | Dilution |
|---|---|
| Human sera | 1/200 |
| Davis Ag | 1/40 |
| Control Ag | 1/40 |

TABLE 11

MONOCLONAL ANTIBODIES HCMV-24, HCMV-25 AND HCMV-1 WERE LABELLED WITH $^{125}$I AND USED IN A MACRIA ASSAY ON A COLLECTION OF 17 HUMAN SERA: 4 WERE KNOWN POSITIVE, 7 WERE KNOWN NEGATIVE AND THE STATUS OF 6 WAS NOT KNOWN PRIOR TO THE EXPERIMENT

Positive/negative antigen

| HCMV IgM+ sera | | HCMV IgM− sera | | HCMV IgM unknown | |
|---|---|---|---|---|---|
| ratios cpm | differential cpm | ratios cpm | differential cpm | ratios cpm | differential cpm |
| 12.0 | 1,632 | 4.1 | 459 | 7.8 | 1,895 |
| 14.3 | 1,838 | 5.0 | 568 | 11.9 | 1,762 |
| 8.9 | 1,171 | 6.3 | 776 | 13.5 | 1,656 |
| 15.9 | 2,140 | 5.5 | 586 | 7.0 | 867 |
| | | 4.9 | 561 | 51.0 | 6,704 |
| | | 4.3 | 557 | | |
| | | 6.7 | 724 | 5.8 | 687 |

TABLE 12

Comparison of the results of "Immunodot" Test for HCMV Ags with previous virus isolated data

| Urine spec. No. | Date | Name | Vol. of sample | IRI Results | RVL-isolation in MRC-5 |
|---|---|---|---|---|---|
| 5096 | | MG | 1.5 | − | + at 16 days p.i. |
| 14045 | | MG | 1.5 | − | + 15 days |
| 13974 | | MG | 1.5 | − | + 19 days |
| 9675 | 6.3.84 | SMcK | 2.5 | +(?)± | + |
| 20302 | 25.5.84 | AS | 1.2 | + | + 7 days |
| 20302 | 25.5.84 | AS | 1.5 | + | + 7 days |
| 19838 | | | 0.4 | − | −ve |
| 18323 | | JR | 1.5 (+ Surbitol) | − | + 12 days |
| 19843 | | | 1.5 | − | −ve |
| 20301 | | AS | 1.4 | + | + 7 days |
| 17124 | | MB | 0.5 | − | + 21 days |
| 19260 | | AS | 1.5 | +(?)± | + 8 days |
| 19842 | | | 1.4 | + | + 16 days |
| 20300 | | AS | 0.8 | + | + 4 days |
| 20010 | | AS | 1.2 | − | + 12 days |
| 20011 | | | 1.4 | − | − |
| 19434 | | | 1.0 | − | − |
| 20186 | | | 1.0 | − | − |
| 20134 | | | 1.0 | − | − |
| 19427 | | | 1.0 | − | − |
| 20282 | | BR | 1.0 | − | + 25 days |

Key:
p.i. = post-infection
RVL = Regional Virus Laboratory, City Hospital, Edinburgh.

We claim:

1. A method for detecting the presence of HCMV-specific IgM in a clinical sample, which comprises:
    capturing IgM in a clinical sample with anti-human IgM immobilized on a support,
    reacting captured IgM with HCMV antigens, and
    detecting the resulting bound HCMV antigens with labelled HCMV-specific monoclonal antibody.

2. A method according to claim 1 wherein a mixture of labelled monoclonal antibodies is used for detecting the resulting bound HCMV antigens.

* * * * *